United States Patent [19]

Densmore et al.

[11] Patent Number: 5,007,904
[45] Date of Patent: Apr. 16, 1991

[54] PLUNGER FOR POWER INJECTOR ANGIOGRAPHIC SYRINGE, AND SYRINGE COMPRISING SAME

[75] Inventors: Larry L. Densmore, Raleigh, N.C.; Thomas A. Lindner, Brookfield, Wis.

[73] Assignee: Coeur Laboratories, Inc., Raleigh, N.C.

[21] Appl. No.: 299,974

[22] Filed: Jan. 19, 1989

[51] Int. Cl.$^5$ ............................................. A61M 5/20
[52] U.S. Cl. ................................. 604/228; 604/218; 128/655
[58] Field of Search ............... 604/218, 228, 187, 154, 604/155; 128/655, 654, DIG. 1; 222/386

[56] References Cited

U.S. PATENT DOCUMENTS

| | | | |
|---|---|---|---|
| 858,025 | 6/1907 | Reese | 604/218 |
| 1,648,308 | 11/1927 | Hofschneider | 604/218 |
| 2,524,367 | 10/1950 | Smith | 604/228 |
| 3,057,351 | 10/1962 | Kimura et al. | 604/218 |
| 4,636,198 | 1/1987 | Stade | 604/154 |
| 4,677,980 | 7/1987 | Reilly et al. | 604/655 |
| 4,677,980 | 7/1987 | Reilly et al. | 128/655 |
| 4,685,910 | 8/1987 | Schweizer | 604/218 |
| 4,705,509 | 11/1987 | Stade | 604/154 |
| 4,906,231 | 3/1990 | Young | 604/110 |
| 4,991,695 | 3/1990 | Lindner | 604/228 |

FOREIGN PATENT DOCUMENTS

| | | | |
|---|---|---|---|
| 195026 | 1/1958 | Austria | 604/218 |
| 2031841 | 1/1973 | Fed. Rep. of Germany | 604/228 |
| 416385 | 10/1910 | France | 604/228 |

*Primary Examiner*—C. Fred Rosenbaum
*Assistant Examiner*—Mark O. Polutta
*Attorney, Agent, or Firm*—Steven J. Hultquist

[57] ABSTRACT

A plunger having a generally converging distal portion, and a rear face on which is provided a coupling structure. The coupling structure is transversely engageable by, and transversely disengageable from, a driving mechanism of a power-driven angiographic syringe, and, one engaged, cannot be disengaged by rotation of the driving mechanism relative to the plunger in the absence of translational movement of the driving mechanism and plunger relative to one another. The coupling structure may include a rearwardly extending wall to which is joined a radially inwardly extending flange. The coupling structure may be generally C-shaped, with a continuously curved portion having an arc length not exceeding about 180°, and optionally may have tangentially extending end segments respectively joined to the continuously curved portions. Such plunger has utility in angiographic syringes of a type employed with power injector means which comprises a driving mechanism with a head engageable with the coupling structure of the plunger.

12 Claims, 3 Drawing Sheets

PLUNGER FOR POWER INJECTOR ANGIOGRAPHIC SYRINGE, AND SYRINGE COMPRISING SAME

BACKGROUND OF THE INVENTION

1. Field of the Invention

This invention generally relates to power-driven angiographic syringes, and specifically to a plunger for such a syringe, and the syringe comprising same.

2. Description of the Related Art

In the field of angiography, a contrast medium of suitable indicating character (radiopacity) is introduced under pressure into coronary arteries, and the arterial network then is monitored by fluoroscopic or other visualizing means. As a result, arterial plaque deposits and/or other arterial occlusions are readily visually determined as to their size and location, so that suitable treatment methods, such as removal of the occuluding material by lasing or mechanical excision, or displacement techniques such as ballon angioplasty, may be carried out.

To effect the introduction of the contrast medium into the arterial network for angiographic study, it has been common practice to utilize injector syringes in combination with arterial catheters. The syringe may be machine-mounted in a so-called "power injector" apparatus, with the distal end of the syringe being connected to the catheter which is introduced into the arterial system to be studied.

There is disclosed in U.S. Pat. No. 4,677,980 issued Jul. 7, 1987 to D. M. Reilly, et al, an angiographic power injector featuring a rotating turret for housing multiple angiography syringes in readiness for injection. In use, the turret is selectively rotated to align an angiographic syringe with a driving mechanism of the power injector. Specifically, as is shown in FIGS. 9 and 10 of this patent, the plunger of the angiographic syringe may be configured with rearwardly extending hook members which are engaged by the head and stem portion (typically termed a "ram" in the field) of the driving mechanism.

In the plunger configuration disclosed in this patent, the hook elements on the proximal face of the plunger are diametrally opposed to one another, to form a slot therebetween through which the ram head is inserted and subsequently rotated, the head being of transversely extending character, so that it thereby engages the respective hook members. In this manner, the head and stem of the driving mechanism and the hook members are described to constitute a quick release driving connection, with the driving mechanism head fitting into the aperture formed by the hook members, and with the stem extending out from the aperture through the access slot between the hook members.

The Reilly et al patent, at column 6, lines 24–52 thereof, describes the subsequent operation of the coupled syringe, as comprising the forward translation of the driving mechanism to drive the plunger through the syringe to expel air therefrom, followed by connection of the syringe to a source of contrast media and retraction of the driving mechanism to pull the plunger back through the syringe, to draw contrast media thereinto, and finally advancement of the driving mechanism to drive the plunger distally in the syringe and effect injection of the contrast media through the catheter attached to the syringe. The patent states that after the injection has been carried out, the driving mechanism may be disengaged from the plunger, without reversing its movement, by the simple expedient of rotating the driving mechanism 90°, so that the driving mechanism head extends from the aperture on either side (see FIG. 10 of the patent). Subsequent retraction of the driving mechanism results in the head and stem of the driving mechanism being withdrawn from the aperture and slot thereby disengaging the driving mechanism from the plunger.

As a result of the foregoing configuration of the driving mechanism, and the hook members on the plunger, the risks incident to retracting the plunger through the syringe during the angioplasty procedure are said to be eliminated, and the mating hook members and driving mechanism head are said to cooperate so that the plunger can be placed in either a driven retractable state, or an undriven non-retractable state, at any time during the injection operation and at any position of the plunger, without substantial force being applied therebetween.

While the foregoing configuration of the hook members on the plunger facilitates the engagement and disengagement of the driving mechanism, without change in the position of the plunger, it also is true that the hook members themselves provide only a very small contact area for mating with the head of the driving mechanism, when the driving mechanism is in driving or retraction engagement with the hook members.

There is thus the danger that the head of the driving mechanism may disengage from contact with the hook members during operation of the syringe, so that subsequent rotation of the driving mechanism to effect disengagement actually effects re-engagement of the driving mechanism with the hook members, in turn causing retraction of the plunger, an occurrence which specifically is desired to be avoided.

The Reilly et al patent discloses other plunger and driving mechanism constructions, e.g., as shown in FIGS. 11–21 of the patent, but all such alternative constructions are relatively more complex in construction and operation.

Accordingly, it would be a substantial advance in the art to provide a plunger construction which is engageable with the driving mechanism of an angiography power injector apparatus, and overcomes the aforementioned deficiencies of the plunger constructions described above.

Accordingly, it is an object of the present invention to provide a plunger which is readily engageable with the driving mechanism of a power injector, and overcomes the aforementioned deficiencies of the prior art plunger and syringe structures.

It is another object of the present invention to provide an angiography syringe comprising such a plunger.

Other objects and advantages of the present invention will be more fully apparent from the ensuing disclosure and appended claims.

SUMMARY OF THE INVENTION

In one aspect, the present invention relates to a plunger for a power-driven angiographic syringe, wherein the plunger comprises a main body including a generally convergent distal portion and a proximal face with driving mechanism (ram-engageable) coupling means thereon. The coupling means on the proximal face of the plunger are transversely (laterally) engageable by and disengageable from the driving mechanism, and, once engaged, the driving mechanism cannot be disengaged from the coupling means by rotation of the driving mechanism relative to the plunger.

In a preferred aspect, the coupling means on the proximal face of the plunger comprise a circumferentially and proximally extending wall joined at a lower extremity thereof to the proximal face of the plunger main body, and a radially inwardly extending flange joined at an outer peripheral portion thereof to a proximal extremity of the wall, the radially inwardly extending flange and wall jointly forming a cavity transversely (laterally) open to insertion of a driving mechanism head thereinto.

Thus, the wall and flange structure forming the cavity may have a generally C-shape in plan view (i.e., when viewed from the longitudinal axis of the plunger body, with the proximal face of the plunger body oriented transversely to such longitudinal axis). Preferably, the wall and flange have a continuously curved arc length which does not exceed about 180°.

The invention relates in another aspect to an angiographic syringe comprising a plunger of the above-described construction.

Other aspects and features of the invention will become more fully apparent from the ensuing disclosure and appended claims.

DETAILED DESCRIPTION OF THE INVENTION, AND PREFERRED EMBODIMENTS THEREOF

Figure 1:
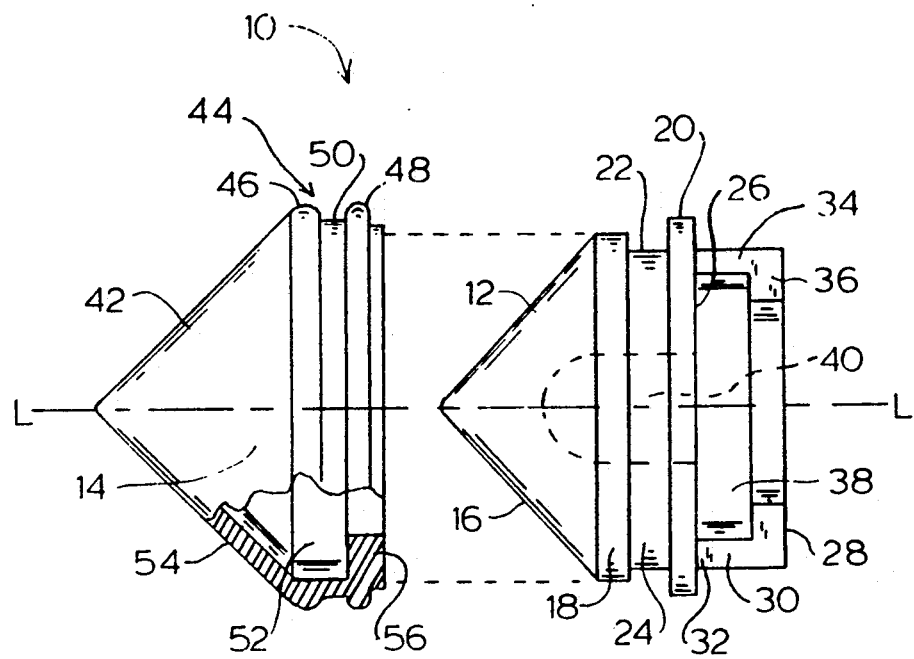
FIG. 1 is an exploded side elevation view of a plunger assembly according to the present invention, in one embodiment thereof.

Referring now to the drawings, there is shown in FIG. 1 a plunger assembly 10 in accordance with one embodiment of the present invention. The plunger assembly shown comprises a plunger body 12 and a frontal sheath 14.

The plunger body 12 of the plunger assembly has a conical distal end portion 16 extending proximally to a distal cylindrical portion 18, rearwardly of which is provided a cylindrical proximal portion 20. The respective distal and proximal cylindrical portions 18 and 20 of the plunger body are in axial spaced relationship to one another. The axis of the plunger assembly and constituent parts is indicated by line L—L in FIG. 1. Between the respective cylindrical portions 18 and 20 is a groove 22, having an interior surface defined by the intermediate cylindrical portion 24 of the plunger body.

The proximal cylindrical portion 20 of the plunger body 12 features a proximal face 26 which preferably is generally planar as shown. Integrally formed with the plunger body 12, as above described, is a coupling structure 28, for coupling of the plunger with the head of a driving mechanism, in a manner which is as more fully described hereinafter.

The coupling structure 28 comprises a circumferentially and proximally extending wall 30 joined at its distal end 32 to the proximal cylindrical portion 20 of the plunger body, at face 26 thereof. At its upper extremity 34, the wall is joined to a flange 36 which extends radially inwardly as shown, thereby forming a cavity 38 with the rear face 26 of the plunger body, into which the head of the driving mechanism may be transversely inserted as hereinafter more fully described.

The plunger body 12 may suitably be formed with a central cavity 40, to minimize weight and material requirements for the plunger, as well as to facilitate molding, by providing faster mold cycling times, when the plunger body is formed of a molded material.

The distal sheath 14 of the plunger is adapted to fit matingly over the distal conical portion 16, and the respective distal and intermediate cylindrical portions 18 and 24, of the plunger body. The distal sheath preferably is formed of resilient material, of sufficient intrinsic lubricity or amenability to lubrication, to yield it slidably engageable with the inner wall surface of a syringe in which the plunger is deployed.

The distal sheath 14 comprises distal conical portion 42 and a proximal portion 44 whose outer surface describes axially spaced-apart ridges 46 and 48 bounding a groove 50 therebetween.

As shown in the broken-away portion 52 of the distal sheath, the sheath wall 54 is of generally uniform thickness along the conical distal portion 42. At its rearward extremity, the sheath wall forms a radially inwardly extending flange 56 which mates cooperatively with the groove 22 of the plunger body, when the sheath and body of the plunger are cooperatively mated with one another.

In general, the plunger body 12 may be formed of any suitable material of construction which is advantageously employed in the use environments of the plunger and the syringe with which the plunger may be associated. The plunger body may for example be formed of a generally stiff, resilient material, such as a hard elastomer, or alternatively, it may be formed of any other suitable natural or synthetic, polymeric or non-polymeric materials. In practice, plastics generally are preferred materials of construction. A polymeric material which may be employed to good advantage in such plunger body is polyphenylene oxide, such as the polyphenylene oxide material commercially available from General Electric Company (Pittsfield, Mass.) under the trademark Valox.

The plunger sheath 14 likewise may be formed of any suitable material which is advantageously employed in the use environments of the plunger and syringes with which same is associated. Preferred materials of construction include rubber materials, with natural rubber typically being most preferred. The sheath is suitably flexible, resilient, and elastomeric in character, to accommodate mating with the plunger body in a manner insuring that the sheath is retained in position on the plunger body during the use of the plunger.

Figure 2:
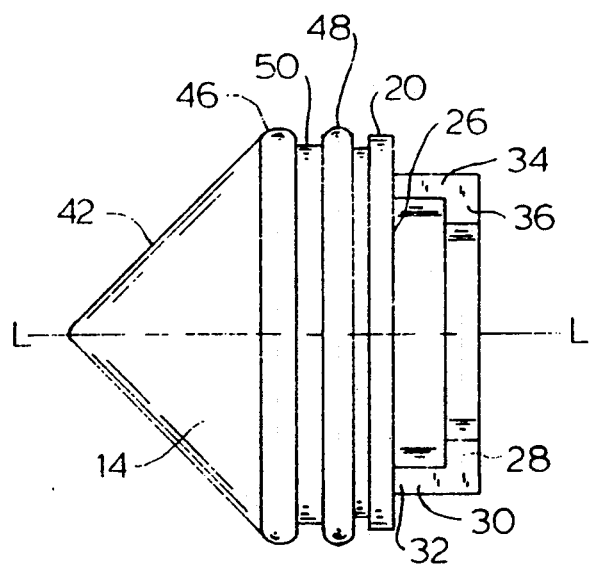
FIG. 2 is a plunger assembly according to the present invention, corresponding to the plunger construction shown in FIG. 1, when assembled.

A side elevation view of a plunger, as assembled from the sheath and body components of FIG. 1, is shown in FIG. 2, wherein all parts and elements are numbered correspondingly with respect to the same or corresponding features in FIG. 1.

Figure 3:
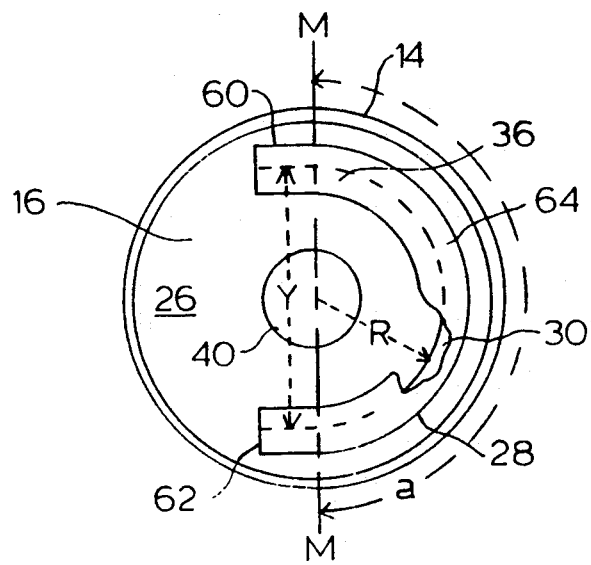
FIG. 3 is a rear elevation view of the plunger assembly of FIG. 2.

FIG. 3 shows a rear elevation view of the plunger of FIGS. 1 and 2, wherein the same parts and features are correspondingly numbered. As shown, the coupling structure 28 comprises the circumferentially and rearwardly extending wall 30, to the upper extremity of which is joined radially inwardly extending flange 36. The coupling structure thus has a C-shape in the plan view shown in FIG. 3, with a continuously curved portion having an arc length of 180°, measured as angle a in FIG. 3, and with peripheral segments 60 and 62 joined to the continuously curved portion. The peripheral segments 60 and 62 are generally tangential with respect to the extremities of the continuously curved portion 64 at this juncture along diametral axis M—M.

A cavity thereby is defined by the coupling structure with the rear surface 26 of the plunger body. The above-described C-shaped configuration of the coupling structure provides a transverse cavity dimension, identified as Y in FIG. 3, which accommodates the lateral insertion of the driving mechanism head into the cavity. The dimension Y in this embodiment this is equal to twice the radius of curvature (identified as R in FIG. 3), of the bounding wall 30 of the coupling means structure 28.

Figure 4:
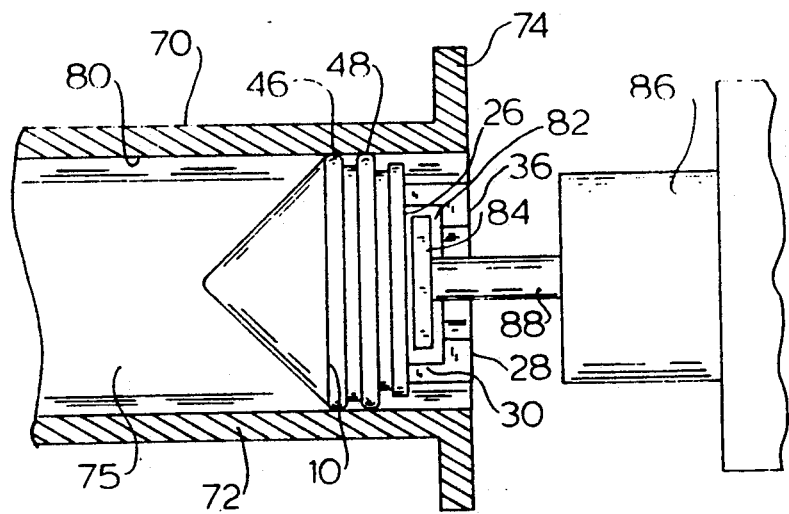
FIG. 4 is a side elevation view, in partial cross-section, of an angiographic syringe comprising a plunger according to one embodiment of the present invention, in operative engagement with power injector means.

FIG. 4 is a side elevation view, in partial section, showing an angiographic syringe comprising the plunger of the present invention, and an associated part of the driving mechanism of an angiography power injector apparatus, in engagement with the plunger.

The angiographic syringe 70 comprises a generally cylindrical barrel 72, which terminates at its proximal end in a circumferentially continuous, radially extending flange 74.

The plunger 10 is reposed in the interior volume 75 of the angiographic syringe 70, with the ridges 46 and 48 of the plunger sheath being in contact with the inner wall surface 80 of the angiographic syringe.

The plunger comprises a coupling structure 28 including circumferentially and rearwardly extending wall 30 and radially inwardly extending flange 36, with the rearwardly extending wall and the radially inwardly extending flange corporately defining with the rear face 26 of the plunger a cavity 82. The cavity 82 is constructed and arranged for receiving the head 84 of driving mechanism 86. The head 84 is mounted on an axially extending shaft 88, and the driving mechanism comprises means (not shown) for axially extending or retracting the shaft 88 and head 82 as desired.

Figure 5:
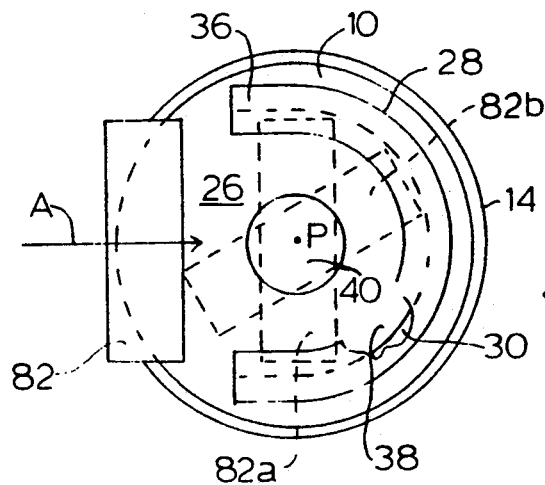
FIG. 5 is a rear elevation view of a plunger according to one embodiment of the present invention, together with the head element of the driving mechanism, showing their coaction.

FIG. 5 shows a rear elevation view of the plunger 10 and the head 82 of the driving mechanism, positioned for engagement of the head with the coupling structure 28, by translation of the head relative to the plunger, in the direction indicated by arrow A (or, alternatively, by translation of the plunger relative to stationary head 82, in a direction opposite to that indicated by arrow A).

Thus, the head 82 and plunger 10 may be translated relative to one another, to bring the head 82 into position in the cavity 38, wherein the head is retained in position against axial movement by the flange 36, and is retained against radial movement along the periphery of the coupling structure 28 by the circumferentially extending wall 30. The head 82 may therefore be transversely inserted into the cavity so that it is placed in the position indicated by the dotted line representation 82a.

Subsequently, so long as the central axis of the driving mechanism is coincident with the central axis of the plunger (the plunger axis being denoted by point P in FIG. 5), subsequent rotation of the driving mechanism relative to the plunger, as for example to the position indicated by the dotted line representation 82c, will not result in disengagement of the head of the driving mechanism from the plunger. In other words, once the driving mechanism has been brought into initial engagement with the coupling structure 28 of the plunger 10, any subsequent rotation of the head and shaft of the driving mechanism will not disengage the plunger from the driving mechanism. This retention feature is at odds with the "quick release" structure described in the aforementioned Reilly et al U.S. Pat. No. 4,677,980, and achieves a significant advantage thereover, in that the occurrence of vibration, or inadvertent rotation of the head and shaft of the driving mechanism which may cause undesirable (e.g., premature) disengagement of the driving mechanism from the plunger in such prior art system, is avoided by the coupling structure in the plunger of the present invention.

Figure 6:
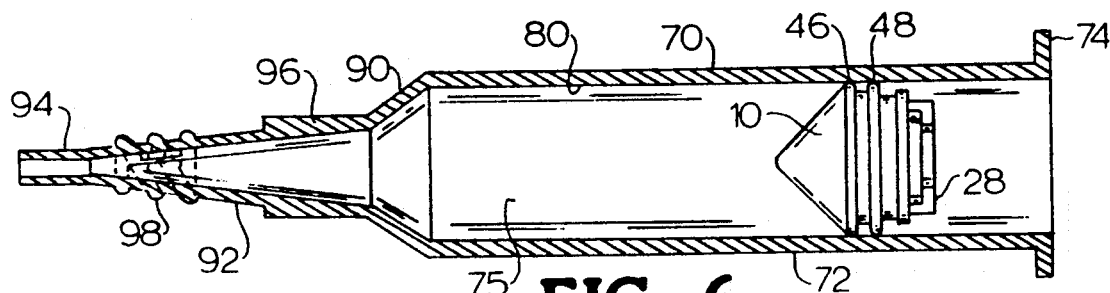
FIG. 6 is a side elevation view, in section, of an angiographic syringe according to the present invention in one embodiment thereof, comprising a plunger in accordance with the present invention.

FIG. 6 is a side elevation view, in section, of an angiographic syringe according to the present invention, in one embodiment thereof, comprising a plunger of the type shown in FIGS. 1-5. The parts and elements in the FIG. 6 angiographic syringe are numbered correspondingly with respect to FIGS. 1-5 hereof, as regards the same or corresponding features therein.

As shown in FIG. 6, the angiographic syringe 70 comprises a generally cylindrical barrel 72 enclosing an interior volume 75 in which the plunger 10 is slidably mounted, in engagement, at ridges 46 and 48, with the inner wall surface 80 of the syringe barrel. The syringe barrel terminates at a proximal end in radially outwardly extending flange 74. At its distal end, the syringe barrel 72 is joined via a frustoconical section 90 to distal tapered section 92, which in turn is joined at a distal extremity thereof to the tubular discharge section 94. The tapered section 92 of the syringe optionally features, at a proximal portion thereof, a plurality of vanes 96, which may be employed for positive locking of the syringe in the mounting structure of a power injector system. The tapered section 92 features on a distal portion of its exterior surface a threading 98, by means of which the angiographic syringe may be coupled, via a suitable complementarily threaded connecting fitting, to an angiography catheter (not shown).

Figure 7:
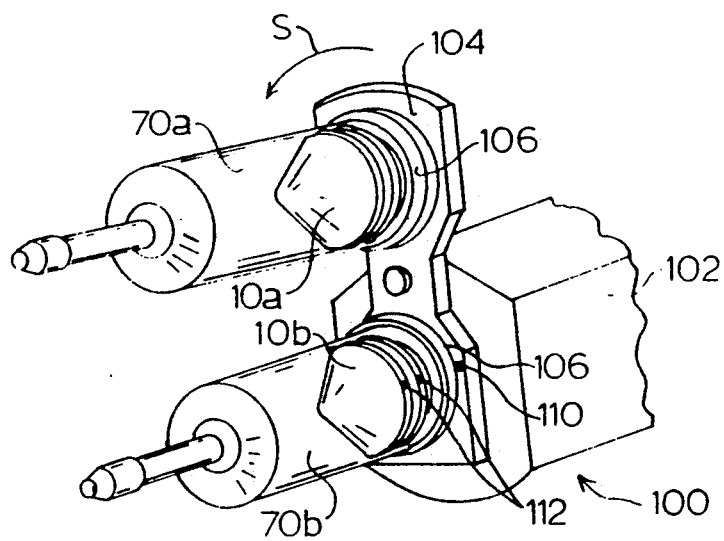
FIG. 7 is a partial perspective view of a power injector device featuring a rotatable carrousel mounting two angiographic syringes in accordance with the present invention.

FIG. 7 is a perspective view of an angiography injection system 100 including power injector 102. The power injector comprises a carrousel 104 mounted for rotation, e.g., in the direction indicated by arrow S in FIG. 7, and contains openings, bounded by collars 106, through which syringes 70a and 70b are inserted. As shown in FIG. 7, the lower syringe 70b has been placed, by selective adjustment of the carrousel, in engagement position with the driving mechanism of the power injector 102, so that the plunger 10b of syringe 70b is placed into engagement with the head and shaft of the driving mechanism as shown in FIG. 4. Concurrently, the angiographic syringe 70a, comprising plunger 10a, is mounted in position on the upper segment of the carrousel, for subsequent translation into alignment with the power injector driving mechanism, and concurrent disengagement of the plunger 10b of syringe 70b therefrom.

In view of the fact that the C-shaped coupling means illustratively described hereinabove with reference to FIGS. 1-6 has a "directional" character, in that the plunger proximal face must be rotationally aligned with the head of the driving mechanism, to permit lateral engagement of the driving mechanism head with the cavity defined by the coupling means with the proximal face of the plunger (see, for example, FIG. 5, wherein the coupling structure 28 has been rotationally aligned to permit lateral engagement with the driving mechanism head 82), with corresponding orientation of the plunger and coupling structure being required for lateral disengagement of the driving mechanism head from the cavity defined by the coupling structure and proximal face of the plunger, the alignment system illustrated in FIG. 7 may be desirable. As shown in that drawing, the carrousel 104 has an alignment mark 110 thereon, with which complementary marks 112 on the adjacent ridges of the plunger 10b are selectively aligned, at the time the syringe and plunger are installed on the carrousel. Plunger 10a and the carrousel 104 are likewise provided with corresponding alignment marks, opposite to the position shown for alignment marks 110 and 112, and thus not visible in the view of FIG. 7.

As an illustrative example of an embodiment of the plunger of the invention, such as may be usefully employed with a 150 milliliter angiographic syringe, the plunger, of a type as shown in the respective drawings of FIGS. 1-7 hereof, may have a body formed of Valox ® polyphenylene oxide (General Electric Company, Pittsfield, Mass.) and a sheath of natural rubber. The conical distal portion 16 of the body comprises surfaces which define with the central axis of the body an included angle of 45°. The diameter of the proximal cylindrical portion 20 of the plunger is 1.59 inch, the diameter of the distal cylindrical portion 18 of the plunger is 1.405 inch, and the diameter of the intermediate cylindrical portion 24 of the plunger is 1.265 inch. The distal cylindrical portion 20 of the plunger in this illustrative embodiment has an axial thickness of 0.125, the intermediate cylindrial portion 24 of the plunger has an axial thickness of 0.18 inch, and the distal cylindrical portion 18 of the plunger has an axial thickness of 0.12 inch.

The rearwardly extending wall 30 of this illustrative embodiment has a radial thickness of 0.12 inch, and the axial distance from the flange surface bounding the cavity 38, to the face 26 of the plunger body, is 0.165 inch. The axial height of the coupling structure 28, as measured axially from the rear face 26 of the plunger body, is 0.335 inch, and the diameter of the cavity 38 is 1.04 inch. With reference to FIG. 3, the arc length a of the continuously curved portion of the coupling structure 28 is 180°, and the radial distance R is 0.52 inch, Y being 1.04 inch, as indicated. The length of each of the peripheral segments 60 and 62, as measured from the center line diameter M—M, to the outer extremity of the respective peripheral segments, is 0.25 inch. The thickness of the rearwardly extending wall 30 is 0.12 inch, and the axial thickness of the flange 36 is 0.17 inch. The diameter of the central opening 40 is 0.562 inch.

While the invention has been described with reference to specific embodiments, aspects, and features thereof, it will be appreciated that the invention is not thus limited, in that apparent variations, modifications, and other embodiments will suggest themselves to those of ordinary skill in the art. Accordingly, the invention is to be broadly construed and regarded as encompassing all such alternative variations, modifications, and embodiments.

What is claimed is:

1. A plunger for a power-driven angiographic syringe, said plunger comprising a body of generally convergent distal profile having a proximal face with ram-engageable coupling structure thereon, said coupling structure comprising a wall extending rearwardly from said proximal face of the plunger body and partially circumferentially thereon, said wall terminating at a proximal extremity, with a radially inwardly extending flange joined at an outer peripheral portion thereof to a proximal extremity of the wall, the radially inwardly extending flange and the wall forming with the proximal face of the plunger body a cavity transversely open to insertion thereinto of a ram head of a driving mechanism for said power-driven angiographic syringe, said coupling structure being transversely engageable by, and transversely disengageable from, said ram head of said driving mechanism for said power-driven angiographic syringe, but once transversely engaged by said ram head, being non-disengageable by rotation of said ram head relative to said plunger, in the absence of any transverse translation of the driving mechanism and plunger relative to one another.

2. A plunger according to claim 1, wherein the plunger body is formed of a polymeric material.

3. A plunger according to claim 1, comprising a sheath mounted on a distal portion of the plunger body.

4. A plunger according to claim 3, wherein the sheath is formed of a natural rubber material.

5. An angiographic syringe, having a plunger according to claim 1 mounted therein, for axial sliding movement of the plunger in an interior volume of the syringe.

6. A plunger for a power-driven angiographic syringe, said plunger comprising a body having a generally converging frontal portion, and a rear face, with a C-shaped coupling structure mounted on said rear face for selective engagement with and disengagement from a ram head of a driving mechanism for said power-driven angiographic syringe, said coupling structure comprising a wall joined to and extending rearwardly from said rear face of the plunger body, and a radially inwardly extending flange joined at an outer periphery thereof to a rearmost extremity of the wall, said coupling structure being transversely engageable by, and transversely disengageable from, said ram head of said driving mechanism for said power-driven angiographic syringe, but, once transversely engaged by said ram head, being non-disengageable by rotation of said ram head relative to said plunger, in the absence of any transverse translation of the driving mechanism and plunger relative to one another.

7. A plunger according to claim 6, wherein the coupling structure comprises a continuously curved portion having an arc length in the vicinity of 180°, and tangentially extending end sections joined to extremities of said continuously curved portion.

8. An angiographic syringe, comprising a plunger according to claim 7.

9. An angiographic power injector system comprising a driving mechanism including head and shaft elements; and an angiographic syringe comprising a plunger according to claim 7, mounted for selective engagement with the head element of the driving mechanism thereof.

10. A syringe plunger for a power-driven angiographic syringe, said plunger having a longitudinal axis and comprising a generally converging distal portion, and a rear face having joined thereto a coupling structure of inverted L-shape, extending circumferentially on said rear face, said coupling structure and said rear face forming a circumferentially and longitudinally bounded cavity, and said coupling structure (a) comprising a continuously curved portion having an arc length not greater than about 180°, and (b) being transversely engageable by, and transversely disengageable from, a ram head of a driving mechanism for said power-driven angiographic syringe, but, once transversely engaged by said ram head, being non-disengageable by rotation of said ram head relative to said plunger, in the absence of any transverse translation of the driving mechanism and plunger relative to one another.

11. A plunger according to claim 10, wherein the coupling structure comprises generally tangential end portions joined to circumferential extremities of said continuously curved portion.

12. A plunger for a power-driven angiographic syringe, said plunger comprising a main body including a generally convergent distal portion and a proximal face with coupling means thereon, said coupling means being transversely engageable by, and transversely disengageable from, a driving mechanism of said power-driven angiographic syringe, but, once transversely engaged by said driving mechanism, being non-disengageable by rotation of said driving mechanism relative to said plunger, in the absence of any transverse translation of the driving mechanism and plunger relative to one another.

* * * * *